United States Patent [19]

Reber et al.

[11] Patent Number: 6,013,513
[45] Date of Patent: Jan. 11, 2000

[54] MOLECULAR DETECTION APPARATUS

[75] Inventors: William L. Reber, Rolling Meadows; John E. Heng, Palatine; Jeffrey G. Toler, Algonquin, all of Ill.

[73] Assignee: Motorola, Inc., Schaumburg, Ill.

[21] Appl. No.: 08/961,111

[22] Filed: Oct. 30, 1997

[51] Int. Cl.[7] .................................................. C12M 1/40
[52] U.S. Cl. .................................... 435/288.5; 435/287.2; 422/72; 422/102
[58] Field of Search ............................ 435/286.5, 287.2, 435/288.5, 288.6, 288.7; 422/64, 68.1, 72, 102

[56] References Cited

U.S. PATENT DOCUMENTS

| | | |
|---|---|---|
| 4,118,280 | 10/1978 | Charles et al. . |
| 4,237,234 | 12/1980 | Meunier . |
| 4,318,994 | 3/1982 | Meyer et al. . |
| 4,767,402 | 8/1988 | Kost et al. . |
| 4,780,212 | 10/1988 | Kost et al. . |
| 4,898,832 | 2/1990 | Klose et al. . |
| 4,948,587 | 8/1990 | Kost et al. . |
| 5,096,670 | 3/1992 | Harris et al. . |
| 5,139,744 | 8/1992 | Kowalski . |
| 5,256,376 | 10/1993 | Callan et al. . |
| 5,472,603 | 12/1995 | Schembri . |
| 5,518,923 | 5/1996 | Berndt et al. . |
| 5,532,128 | 7/1996 | Eggers et al. . |
| 5,565,324 | 10/1996 | Still et al. . |
| 5,589,350 | 12/1996 | Bochner . |
| 5,593,838 | 1/1997 | Zanzucchi et al. . |
| 5,653,939 | 8/1997 | Hollis et al. . |
| 5,707,818 | 1/1998 | Chudzik et al. . |
| 5,736,332 | 4/1998 | Mandecki . |

OTHER PUBLICATIONS www.labfocus.com/biochem/labfeat.htm (1996).
www.labfocus.com/abc/STAFEA.htm (1996).
www.awaretech.com/Identi–Link.html (No date provided).
www.labfocus.com/biochem/labotech.htm (1996).
www.sanguin.com/M2000.HTM (1996).
www.sanguin.com/INFORM.HTM (1996).
www.packardinst.com/m–probe.htm (No date provided).
www.packardinst.com/mp204–bc.htm (No date provided).
Wiedmann, et al., "Ligase Chain Reaction (LCR)—Overview and Application", *PCR Methods and Applications*, S51–S64. (1994).
Barany, F., "Genetic disease detection and DNA amplification using cloned thermostable ligase", *Proc. Natl. Acad. Sci. USA*, vol. 88, pp. 187–193, Jan. 1991.
Barany, et al., "Cloning, overexpression and nucleotide sequence of a thermostable DNA ligase–encoding gene", *Gene*, 109 (1991) pp. 1–11.
Belgrader et al., "A Multiplex PCR–Ligase Detection Reaction Assay for Human Identity Testing", *Genome Science & Technology*, vol. 1, No. 2, 1996, pp. 77–87.
Day, et al., "Detection of Steroid 21–Hydroxylase Alleles Using Gene–Specific PCR and a Multiplexed Ligation Detection Reaction", *Genomics*, 29, pp. 152–162, 1995.
Barany, F., "Two–codon insertion mutagenesis of plasmid genes by using single–stranded hexameric oligonucleotides", *Proc. Natl. Acad. Sci. USA*, vol. 82, pp. 4202–4206, Jun. 1985.

(List continued on next page.)

*Primary Examiner*—William H. Beisner
*Attorney, Agent, or Firm*—James E. Gauger; Jeffrey G. Toler

[57] ABSTRACT

An apparatus comprises a disk-shaped support member (20) supporting a first sample-processing device (28) and a second sample-processing device (30). The first sample-processing device (28) has an elongate portion oriented along a first radial axis (32) of the support member (20). The second sample-processing device (30) has an elongate portion oriented along a second radial axis (34) transverse to the first radial axis (32). A sample-processing device can comprise a plurality of conduits (150) interconnected in a tree topology to couple an inlet (152) with a plurality of outlets (154). The inlet (152) is located at a root vertex and each of the outlets (154) is located at a corresponding leaf vertex of the tree topology. Each of a plurality of molecular detection chambers (156) is coupled to a respective one of the outlets (154). A method of using the apparatus is disclosed.

13 Claims, 8 Drawing Sheets

OTHER PUBLICATIONS

Barany, F., "Directional transport and integration of donor DNA in *Haemophilus influenzae* transformation",*Proc. Natl. Acad. Sci. USA*, vol. 80, pp. 7274–7278, Dec. 1983.

Mayer, et al., "Interaction of TawI Endonuclease with the Phosphate Backbone", *The Journal of Biological Chemistry*, vol. 269, No. 46, Nov. 18, 1994, pp. 29067–29076.

"A Ligase–Mediated Gene Detection Technique", California Institute of Technology, Div. of Biology, Pasadena, CA, vol. 241, dated Aug. 26, 1988, pp. 1077–1080.

"Automated DNA diagnostics using an ELISA–based oligonucleotide ligation assay", publisher Proc. Natl. Acad. Science USA, vol. 87, pgs. 8923–8927, Nov. 1990.

"DNA sequencing by hybridization to microchip octa–and decanucleotides extended by stacked pentanucleotides", 1996 Oxford University Press, Nucleic Acids Research, vol. 24, No. 15 pp. 2998–3004.

"A method for DNA sequencing by hybridization with oligonucleotide matrix", 1991 Harwood Acad. Publishers GmbH, DNA Sequencing and Mapping,vol. 1, pp. 375–388.

"Sequence analysis by hybridization with oligonucleotide microchip: identification of B–Thalassemia mutations", publisher Elsevier Science B.V., Dec. 23, 1996, Gene #10369, 10 pgs. total.

1989 Plenum Publishing Corporation pp. 436–438 "A new method for determining the DNA Nucleotide sequence by hybridization with oligonucleotides", (V.A. Engel'gardt Institute of Molecular Biology, Academy of Seiences of the USSR, Moscow. Translated from Doklady Akademii Nauk SSSR, vol. 303, No. 6 pp. 1508–1511, Dec. 1988.)

"Theoretical analysis of the kinetics of DNA hybridization with Gel–Immobilized Oligonucleotides", Biophysical Journal, vol. 71, Nov. 1996, pp. 2795–2801.

"Regioselective immobilization of short oligonucleotides to acrylic copolymer gels", Nucleic Acids Research, 1996, vol. 24, No. 16, pp. 3142–3148.

"Chemical methods of DNA and RNA fluroescent labeling", Oxford University Press, Nucleic Acids Research, 1996, vol. 24, No. 22, pp. 4535–4532, Sep. 1996.

"Partial Thermodynamic Parameters for Prediction Stability and Washing Behavior of DNA Duplexes Immobilized on Gel Matrix", Journal of Biomolecular Structure & Dynamics, ISSN 0739–1102, vol. 14, issue No. 1 (1996), Adenine Press.

"An oligonucleotide hybridization approach to DNA sequencing", Elsevier Science Publishers B.V. (Biomedical Division) 1989 Federation of European Biochemical Societies, vol. 256, No. 1.2, pp. 118–122.

"Methidium Intercalator Inserted into Synthetic Oligonucleotides", 1996 Elsevier Science Ltd., Tetrahedron Letters, 1996, vol. 37, No. 47, pp. 8467 to 8470.

MOLECULAR DETECTION APPARATUS

RELATED APPLICATIONS

The present application is related to the following applications:

"Binding Assay Methods and Systems", having Attorney Docket No. MNE00519 and Ser. No. 08/846,389 filed Apr. 30, 1997, now U.S. Pat. No. 5,935,785; and "Binding Assays", having Attorney Docket No. MNE00518 and Ser. No. 08/846,907, filed Apr. 30, 1997.

The subject matter of the above-listed applications is hereby incorporated by reference into the disclosure of the present application.

TECHNICAL FIELD

The present invention relates to methods and systems for molecular detection.

BACKGROUND OF THE INVENTION

Recent efforts have been directed in developing chips for molecular detection. Of particular interest are DNA chips for sequencing and diagnostic applications. A DNA chip includes an array of chemically-sensitive binding sites having single-stranded DNA probes or like synthetic probes for recognizing respective DNA sequences. The array of binding sites is typically arranged in a rectangular grid.

A sample of single-stranded DNA is applied to the binding sites of the DNA chip. The DNA sample attaches to DNA probes at one or more of the binding sites. The sites at which binding occurs are detected, and one or more molecular structures within the sample are subsequently deduced.

In sequencing applications, a sequence of nucleotide bases within the DNA sample can be determined by detecting which probes have the DNA sample bound thereto. In diagnostic applications, a genomic sample from an individual is screened with respect to a predetermined set of probes to determine if the individual has a disease or a genetic disposition to a disease.

Many diagnostic devices and methods perform an invasive test requiring a blood sample to be extracted from an end user. For example, most commercially-available portable blood glucose meters require an end user to prick his/her finger with a lancet to perform a blood glucose level test. After pricking his/her finger, the end user deposits a drop of blood onto a test strip. The sample of blood on the test strip is tested by the glucose meter to determine a glucose level. Since a typical end user with diabetes performs the above-described invasive test four times a day, the need exists for a noninvasive apparatus to perform blood glucose level tests.

HIV testing is another diagnostic procedure which uses an invasively-extracted sample of blood. This procedure and other diagnostic procedures also would benefit from a noninvasive apparatus designed therefor.

BRIEF DESCRIPTION OF THE DRAWINGS

The invention is pointed out with particularity in the appended claims. However, other features of the invention are described in the following detailed description in conjunction with the accompanying drawings in which:

DETAILED DESCRIPTION OF A PREFERRED EMBODIMENT

Figure 1:
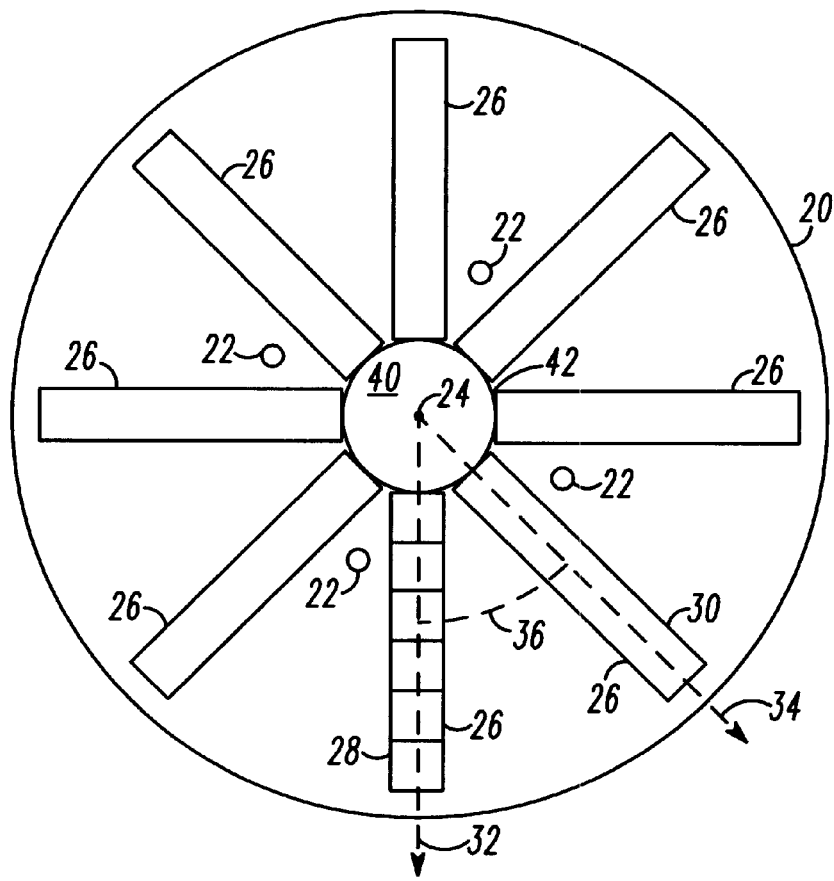
FIG. 1 is a top view of a first embodiment of an apparatus in accordance with the present invention.
Figure 2:
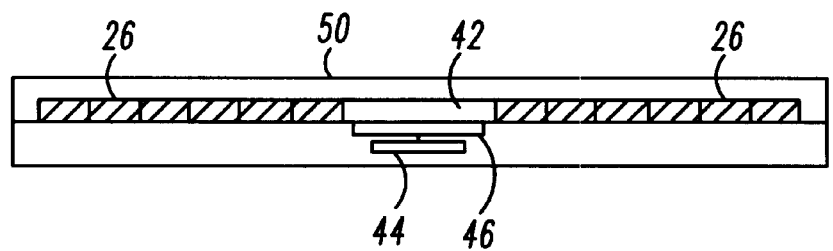
FIG. 2 is a cross-sectional, side view of the apparatus of FIG. 1.

FIGS. 1 and 2 are a top view and a cross-sectional side view, respectively, of a first embodiment of an apparatus in accordance with the present invention.

The apparatus comprises a support member 20 which, preferably, is disk-shaped. The support member 20 includes a plurality of holes 22 to receive a corresponding plurality of pins associated with a rotary positioning device. Preferably, the holes 22 are arranged equidistantly from a center point 24 of the support member 20. Further, it is preferred that adjacent pairs of the holes 22 be separated equidistantly.

The apparatus further comprises a plurality of sample processing devices 26, including a first sample processing device 28 and a second sample processing device 30. The sample processing devices 26 are supported by the support member 20. The sample processing devices 26 can be patterned or fabricated directly onto the support member 20. Alternatively, each of the sample processing devices 26 can be fabricated onto a substrate, such as a strip, for mounting to the support member 20.

Preferably, each of the sample processing devices 26 has an elongate portion oriented along a radial axis of the support member 20. In this case, the elongate portion has a major dimension (i.e. a dimension having a greater length than its other dimensions) oriented either parallel to or substantially parallel to a radial axis of the support member. By substantially parallel, it is meant that the major dimension is closer to being parallel to the radial axis than being perpendicular to radial axis.

The first sample processing device 28 has an elongate portion oriented along a first radial axis 32. The second sample processing device 30 has an elongate portion oriented along a second radial axis 34. The first radial axis 32 is transverse to the second radial axis 34.

The first radial axis 32 and the second radial axis 34 are separated by an angle 36. Preferably, all adjacent pairs of the sample processing devices 26 are separated by angles substantially equal to the angle 36.

The first radial axis 32 and the second radial axis 34 intersect at a central portion 40 of the support member 20. Preferably, the first radial axis 32 and the second radial axis 34 intersect at the center point 24 within the central portion 40 of the support member 20.

Optionally, the apparatus includes a noninvasive extraction device 42 having at least a portion located at the central portion 40 of the support member 20. The noninvasive extraction device noninvasively extracts a biological sample from an end user. Examples of the biological sample include, but are not limited to, blood from the end user and an interstitial fluid from the end user.

Preferably, the noninvasive extraction device 42 extracts the sample through the skin of the end user by transdermal permeation. Alternatively, the noninvasive extraction device 42 can extract the sample through a buccal membrane by transbuccal permeation. Regardless of where the sample is extracted, the noninvasive extraction device 42 extracts the sample without penetrating the skin or another portion of the end user's body.

Preferably, the noninvasive extraction device 42 includes a signal generator 44 and a transducer 46. The signal generator 44 drives the transducer 46 to produce acoustic pressure waves. The acoustic pressure waves enhance and control the permeation of the sample out of the end user's body.

In accordance with the teachings in U.S. Pat. Nos. 4,767, 402, 4,780,212, 4,948,587 which are hereby incorporated by reference into this disclosure, it is preferred that the transducer 46 includes an ultrasonic emitter. In this case, the ultrasonic emitter emits an ultrasonic signal having a frequency between 20 kHz and 10 MHz, with a preferred range being between 0.5 MHz and 1.5 MHz. Further, the intensity of the ultrasound signal is selected so as not to burn the end user. In general, the ultrasonic emitter can emit either a pulsed or a continuous ultrasonic signal.

Upon extracting the sample, a cover 50 is mounted to the support member 20. The cover 50 cooperates with the support member 20 to enclose the sample and the sample processing devices 26 within the apparatus. Preferably, the cover 50 snaps onto the support member 20.

The sample is communicated to each of the sample processing devices 26 by a rotation-induced centrifugal force. Preferably, the aforementioned rotary positioning device rotates the apparatus to create the centrifugal force. The sample is communicated through each of the sample processing devices 26 by the centrifugal force.

Optionally, the apparatus is shaped and sized as a compact disk. In this case, the diameter of the support member 20 and the cover 50 is about 4.75 inches.

Figure 3:
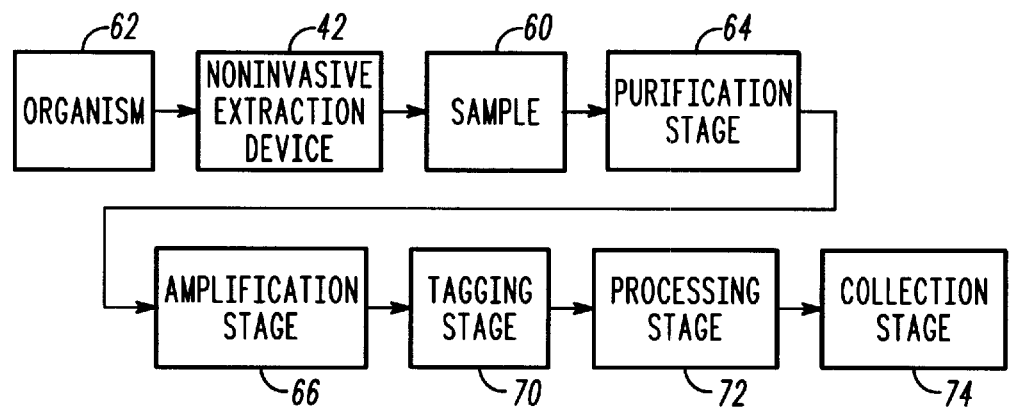
FIG. 3 is a block diagram of an embodiment of a sample processing device.

FIG. 3 is a block diagram of an embodiment of a sample processing device. The sample processing device receives a sample 60. Examples of the sample 60 include but are not limited to a ligand sample, a nucleic acid sample, a genomic sample from an organism 62 or a plant, and an environmental sample. Of particular interest is where the sample includes a sequence of at least one nucleotide base. In this case, the sample can include at least one polynucleotide molecule such as DNA or RNA. Optionally, the sample 60 is noninvasively extracted from the organism 62, such as a human, using the noninvasive extraction device 42.

The sample processing device includes a series of stages to process the sample 60. The series of stages processes the sample in a linear, sequential, and segmented manner. Material can be passively transported from stage to stage using a centrifugal force induced by rotating the apparatus. In this case, it is preferred that the sample 60 is transported unidirectionally, i.e. with no return or feedback to a previous stage. Alternatively, material can be actively transported between stages by generating an electric field or a magnetic field in the sample processing device. The use of actively generated fields is amenable for bidirectional transport of the material.

Preferably, the series of stages includes a purification stage 64, an amplification stage 66, a tagging stage 70, a processing stage 72, and a collection stage 74. The functionality of each of the stages can be either programmable or fixed.

The purification stage 64 performs sample preparation steps such as purifying DNA from cellular material in the sample 60. The amplification stage 66 amplifies the purified sample from the purification stage. The amplification stage 66 can perform a polymerase chain reaction (PCR), for example, to amplify a DNA sample. The PCR process can be modified to cycle a rotation-induced centrifugal force, rather than cycling a temperature, to repeatedly dissociate hybridized molecules.

The optional tagging stage 70 performs a step of applying members to the sample molecules to assist in their detection. Such members are commonly referred to in the art as tags, markers, reporters, and labels. Examples of such members include, but are not limited to, radioactive members, optical members (such as fluorescent members, luminescent members, and light-scattering members), charged members, and magnetic members.

The processing stage 72 performs an assay with the sample. The assay can include a hybridization assay, a ligation assay, an electrophoresis assay, and/or an electroosmosis assay. Preferably, the processing stage 72 includes a chamber within which at least one result of the assay is externally detectable. To allow optical signals to communicate between an external device and the chamber, at least a portion of the cover 50, at least a portion of the processing stage 72, and/or at least a portion of the support member 20 can be transparent.

Waste material from the processing stage 72 is collected in the collection stage 74. Preferably, the collection stage 74 comprises a chamber within which material is externally detectable. To allow optical signals to communicate between an external device and the chamber, at least a portion of the cover 50, at least a portion of the processing stage 72, and/or at least a portion of the support member 20 can be transparent.

Figure 4:
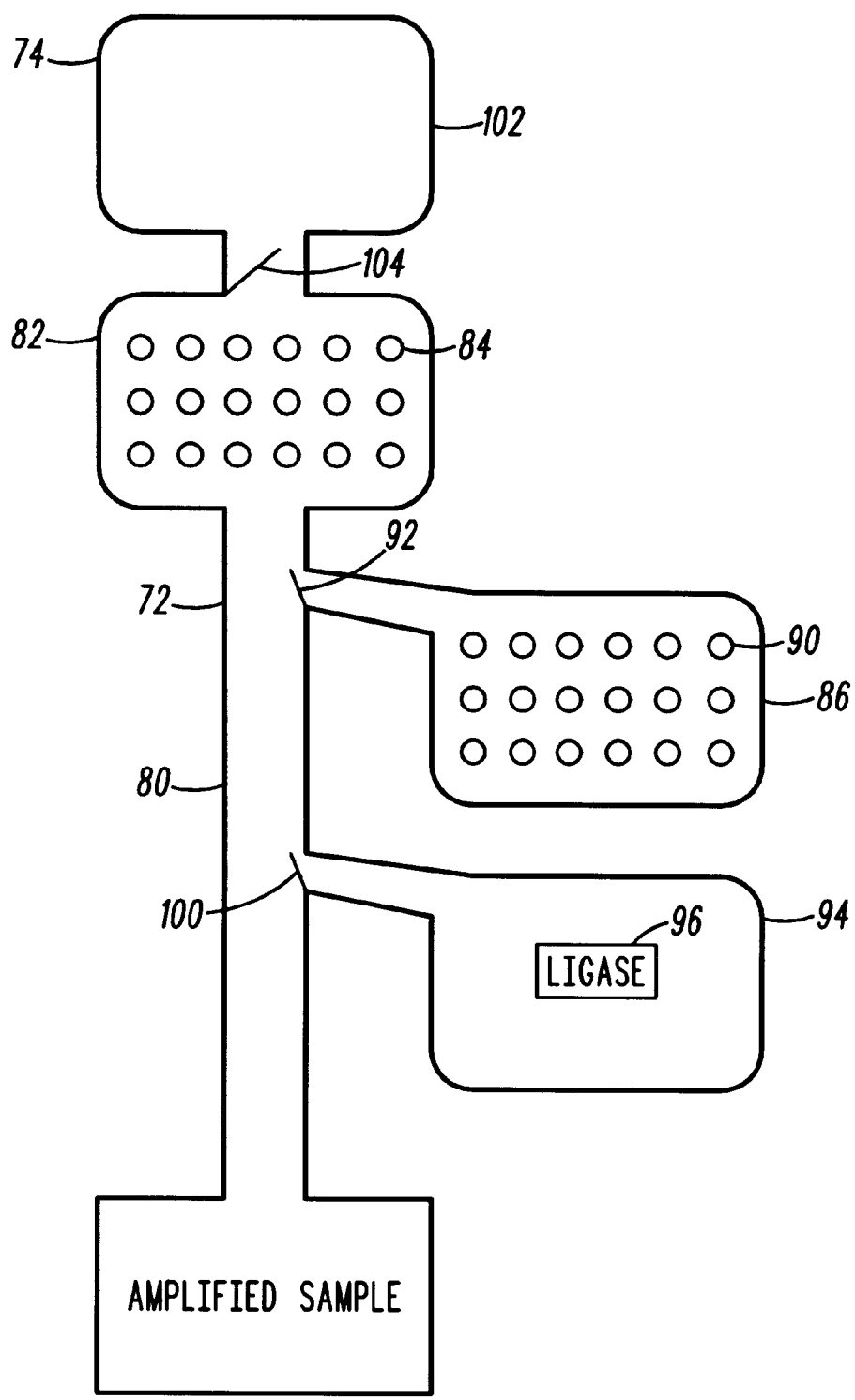
FIG. 4 is a schematic diagram of an embodiment of the processing stage and the collection stage.

FIG. 4 is a schematic diagram of an embodiment of the processing stage 72 and the collection stage 74. The processing stage 72 includes a conduit 80 which receives a plurality of molecules based upon the sample. A chamber 82 containing a plurality of molecular probes 84 is coupled to the conduit 80. Preferably, the molecular probes 84 are immobilized within a region defined by the chamber 82. For example, the molecular probes 84 can have an end which is bound to a surface in the chamber 82.

A chamber 86 containing a plurality of molecular probes 90 is coupled to the conduit 80. Preferably, the molecular probes 90 are tagged with an optical tag. The molecular probes 90 are selectively uncoupled and coupled into the conduit 80 by a gate 92 such as a valve.

A chamber 94 containing ligase 96 is coupled to the conduit 80. The ligase 96 can comprise either a thermal-stable ligase or a non-thermal-stable ligase. A gate such as a valve 100 selectively uncouples and couples the ligase 96 into the conduit 80.

The collection stage 74 comprises a chamber 102 which defines a waste collection region. The chamber 102 is in communication with the chamber 82. Optionally, a gate such as a valve 104 selectively uncouples and couples the chamber 102 with the chamber 82.

Figure 5:
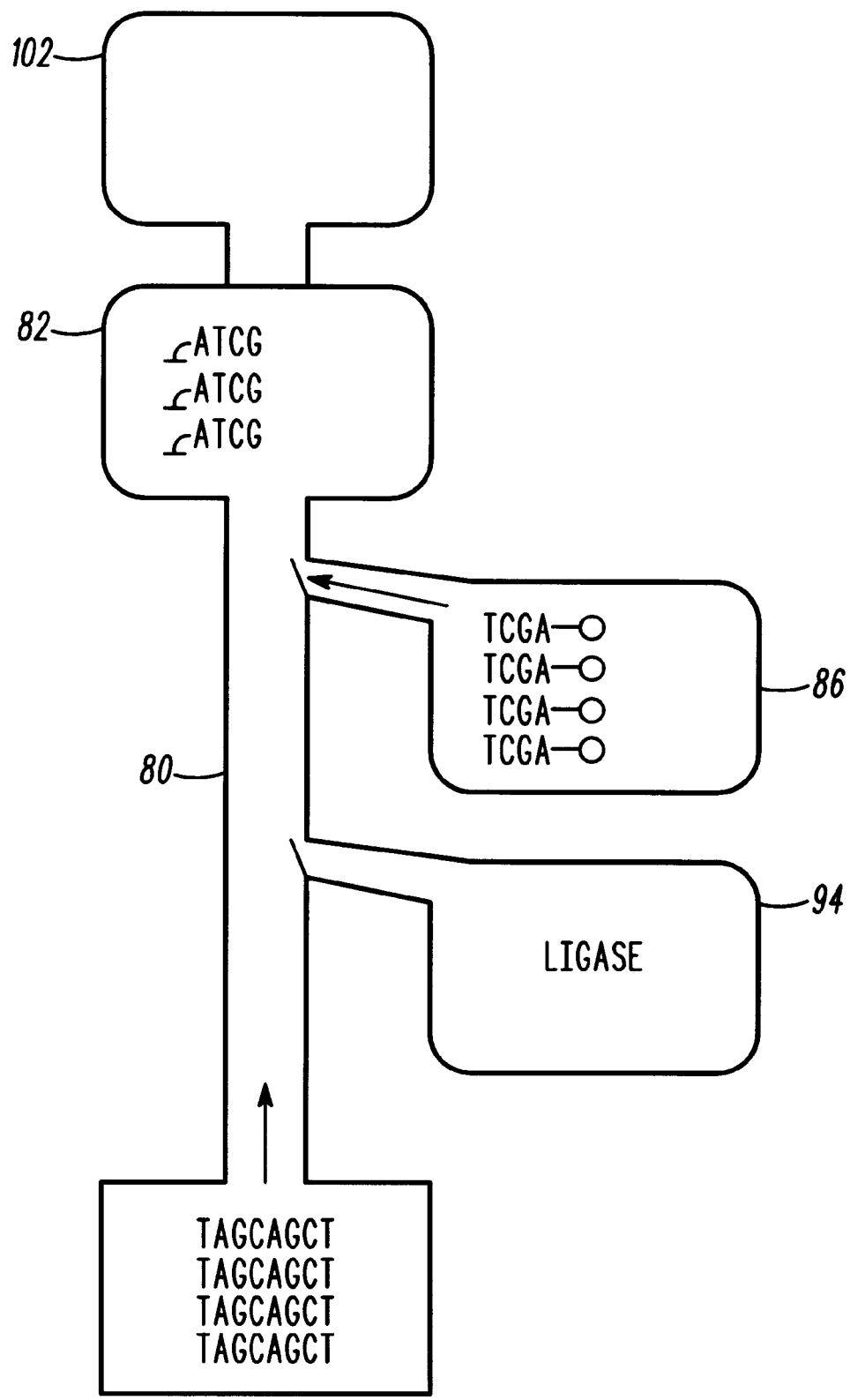
FIGS. 5 to 7 are schematic diagrams of an example of the processing stage and the collection stage at three instances in time.
Figure 6:
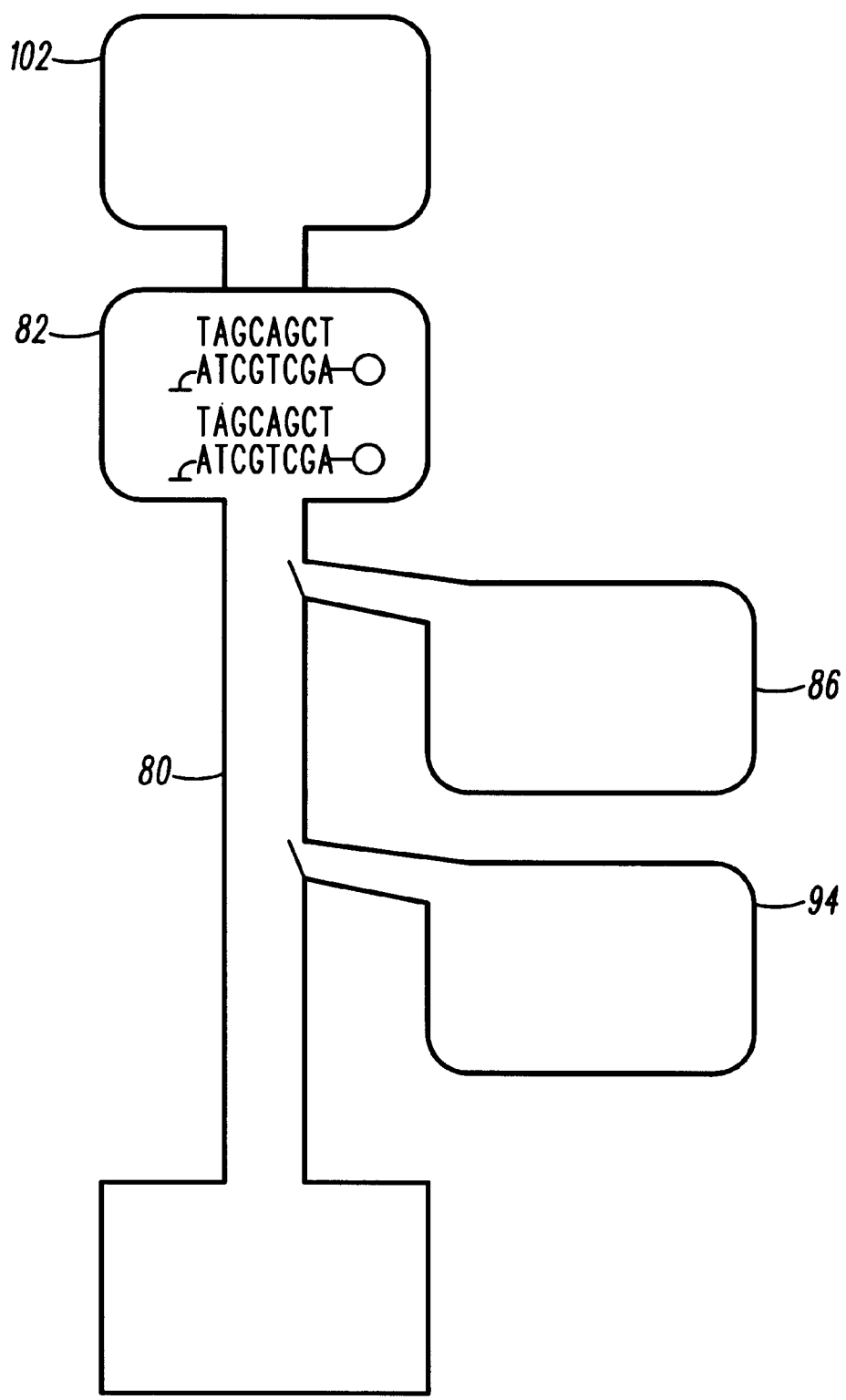
Figure 7:
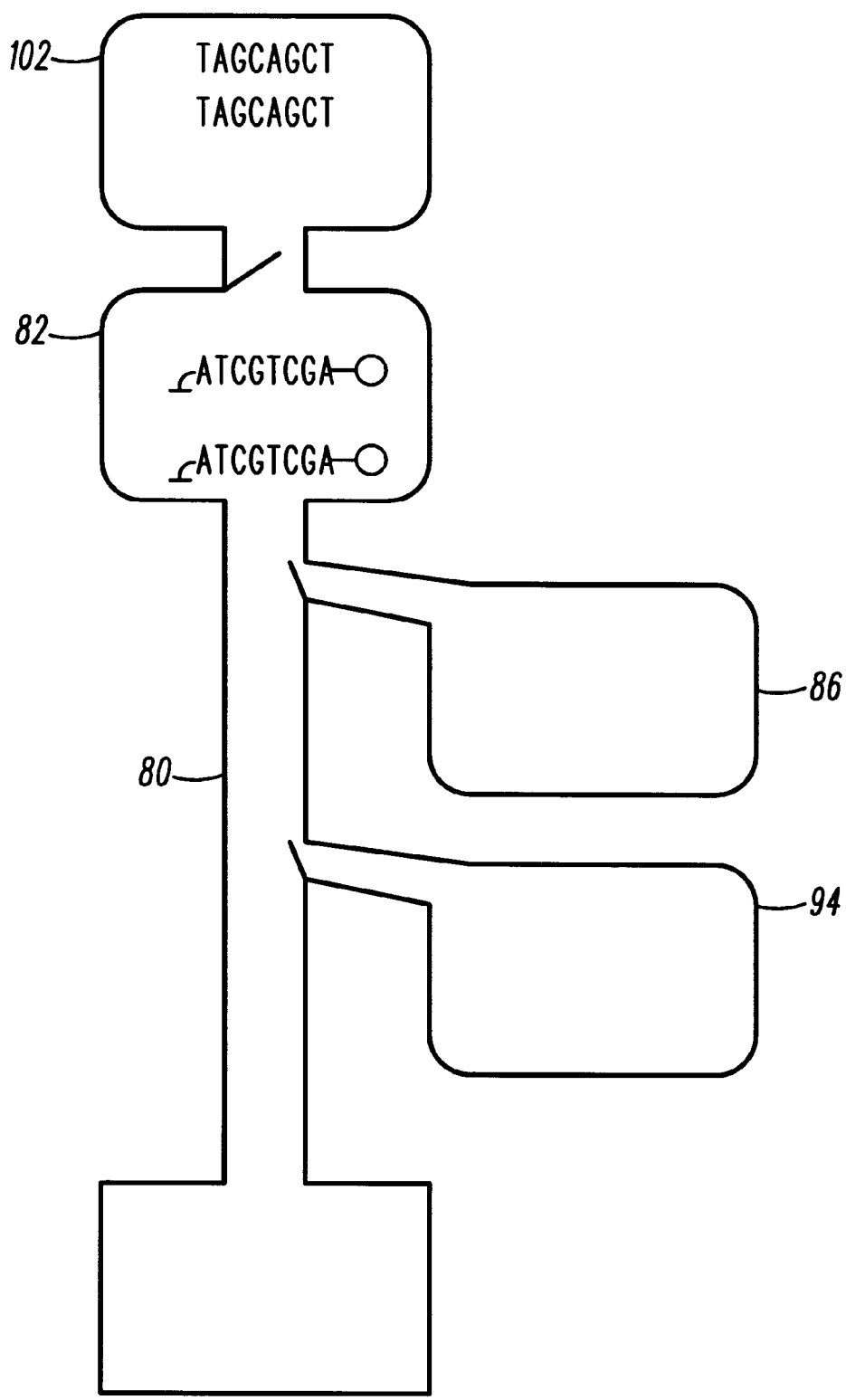

FIGS. 5 to 7 are schematic diagrams of an example of the processing stage 72 and the collection stage 74 at three instances in time. At a first instance in time as shown in FIG. 5, the chamber 82 contains immobilized molecular probes having an A-T-C-G base sequence, the chamber 86 contains tagged molecular probes having a T-C-G-A base sequence, and the sample molecules have a T-A-G-C-A-G-C-T base sequence. (In accordance with standard nucleotide abbreviations, "A" denotes adenine, "C" denotes cytosine, "G" denotes guanine, and "T" denotes thymine.)

Thereafter, the sample molecules, the tagged molecular probes, and the ligase are transported to the chamber 82. Preferably, the sample molecules, the tagged molecular probes, and the ligase are transported in response to a rotation-induced centrifugal force.

At a second instance in time (as shown in FIG. 6): (i) a T-A-G-C portion of the sample molecules binds to the immobilized molecular probes; (ii) the tagged molecular probes bind to a A-G-C-T portion of the sample molecules; and (iii) the ligase links the tagged molecular probe to the immobilized molecular probe bound to a common one of the sample molecules. Thereafter, the sample molecules are dissociated from the ligated molecular probes. The sample molecules can be dissociated either electrically, thermally, or centrifugally. Dissociated sample molecules and unligated ones of the tagged molecular probes are communicated to the chamber 102.

At a third instance in time (as shown in FIG. 7), the chamber 82 contains immobilized, ligated molecular probes, and the chamber 102 contains dissociated sample molecules and the unligated ones of the tagged molecular probes. A result of the assay can be determined by sensing for tagged molecular probes in the chamber 82 and/or the chamber 102.

Figure 8:
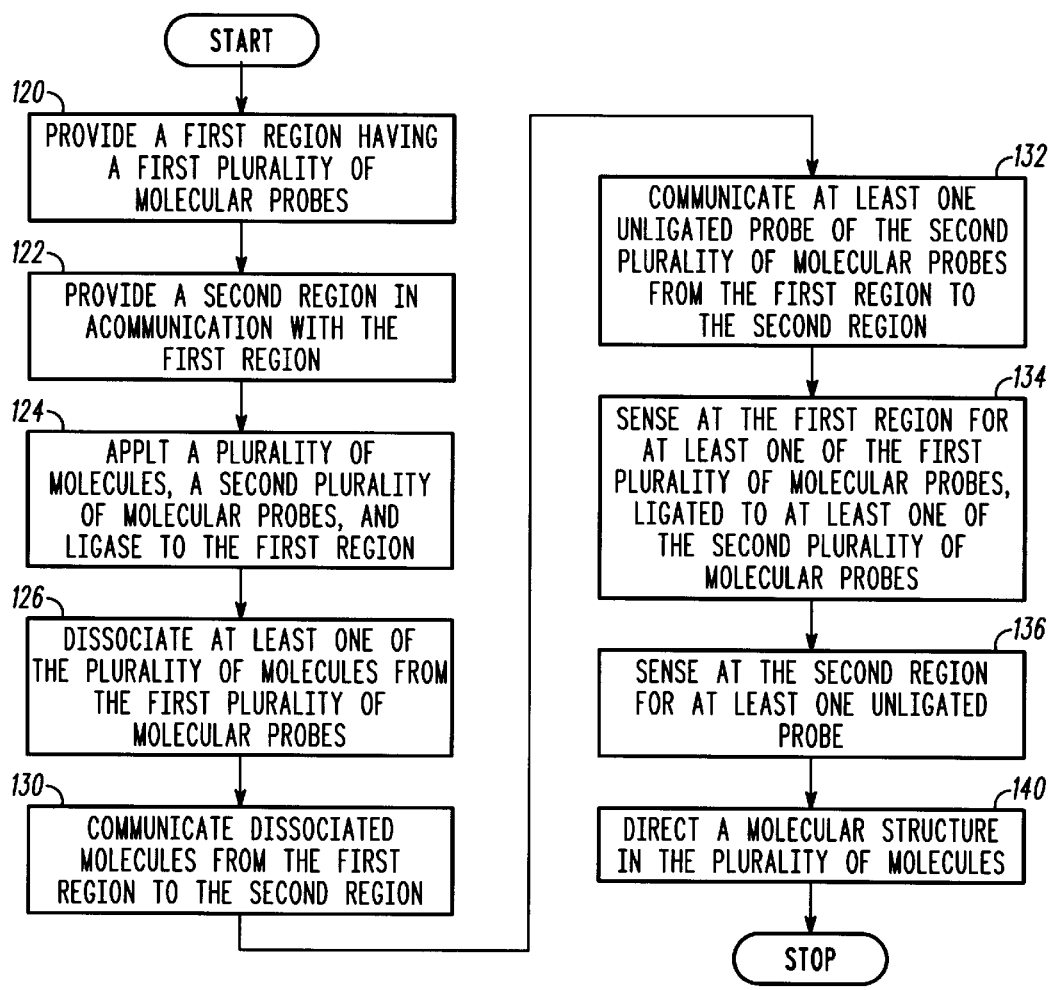
FIG. 8 is a flow chart of an embodiment of a molecular sensing method.

FIG. 8 is a flow chart of an embodiment of a molecular sensing method. Preferably, the method is performed using embodiments of the molecular sensing apparatus described herein. It is noted, however, that the method also can be performed using an alternative apparatus.

As indicated by blocks 120 and 122, the method includes steps of providing a first region having a first plurality of molecular probes and providing a second region in communication with the first region is performed. Preferably, the first region is defined within the chamber 82 and the second region is defined within the chamber 102. It is also preferred that the first plurality of molecular probes be immobilized at the first region.

As indicated by block 124, the method includes a step of applying a plurality of molecules, a second plurality of molecular probes, and ligase to the first region. Preferably, the second plurality of molecular probes are tagged as described earlier.

If the first plurality of molecular probes have an affinity to the plurality of molecules, a step of binding at least one of the plurality of molecules to at least one of the first plurality of molecular probes results. If the second plurality of molecular probes have an affinity to the plurality of molecules, a step of binding at least one of the second plurality of molecular probes to at least one of the plurality of molecules results. If a first molecular probe and a second molecular probe adjacently bind to a molecule, then a step of ligating the second molecular probe to the first molecular probe results.

As indicated by block 126, the method includes a step of dissociating at least one of the plurality of molecules from the first plurality of molecular probes. The molecules can be dissociated either electrically, thermally, or centrifugally.

As indicated by block 130, the method includes a step of communicating dissociated molecules from the first region to the second region. The dissociated molecules can be communicated or transported to the second region either centrifugally or electrophoretically.

As indicated by block 132, the method includes a step of communicating at least one unligated probe of the second plurality of molecular probes from the first region to the second region. The at least one unligated probe can be communicated or transported to the second region either centrifugally or electrophoretically. Typically, the steps indicated by blocks 130 and 132 are performed concurrently by generating a centrifugal force or an electric field to transport unbound molecules.

As indicated by block 134, the method includes a step of sensing at the first region for at least one of the first plurality of molecular probes ligated to at least one of the second plurality of molecular probes. Preferably, this step includes sensing for tags associated with the second plurality of molecular probes.

Optionally, as indicated by block 136, a step of sensing at the second region for the at least one unligated probe is performed. It is preferred that this step includes sensing for tags associated with the second plurality of molecular probes.

As indicated by block 140, a step of detecting a molecular structure in the plurality of molecules is performed. The molecular structure is detected based upon signals or quantities sensed at the first region and optionally the second region. The presence of tags in the first region can indicate that the molecules include a nucleotide base sequence complementary to a first nucleotide base sequence in the first plurality of molecular probes concatenated with a second nucleotide base sequence in the second plurality of molecular probes. The presence of tags in the second region can indicate the contrary.

Optionally, the molecular structure is detected by a differential measurement made between the first region and the second region. For example, if the presence of tags in the first region is significantly greater than the presence of tags in the second region, then the molecular structure is detected. If the presence of tags in the first region is not significantly greater (e.g. is slightly greater than, is approximately equal to, or is less than) than the presence of tags in the second region, then the detection result is insignificant.

Figure 9:
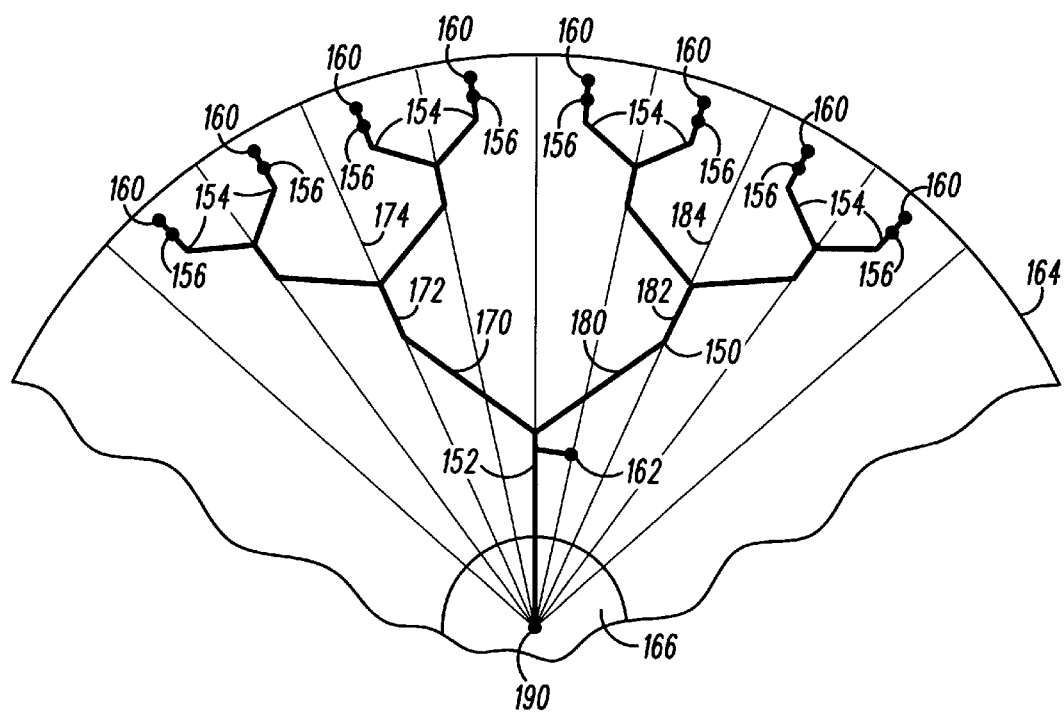
FIG. 9 is an illustration of another embodiment of the processing stage and the collection stage in a molecular detection apparatus.

FIG. 9 is an illustration of another embodiment of the processing stage 72 and the collection stage 74 in a molecular detection apparatus. The teachings given with reference to FIG. 9 can be combined with any of the teachings herein to form alternative embodiments of methods and systems for molecular detection.

A plurality of conduits 150 are interconnected in a tree topology to couple an inlet 152 to a plurality of outlets 154. The conduits 150 provide a plurality of branches of the tree topology. The inlet 152 is located at a root vertex of the tree topology. Each of the outlets 154 is located at a corresponding leaf vertex of the tree topology.

Typically, the tree topology has a height of at least two. For example, FIG. 9 illustrates a tree topology having a height of three. Further, it is typical for the outlets 154 to include at least four outlets, and optionally, at least six outlets. The example of FIG. 9 illustrates eight outlets.

The apparatus includes a plurality of molecular detection chambers 156. Each of the molecular detection chambers 156 is coupled to a respective one of the outlets 154. The apparatus further includes a plurality of chambers 160 each coupled to a respective one of the molecular detection chambers 156. A ligase chamber 162 is coupled to at least one of the conduits 150.

A disk-shaped member 164 supports the conduits 150, the inlet 152, the outlet 154, the molecular detection chambers 156, the chambers 160, and the ligase chamber 162. Optionally, a noninvasive extraction device 166 in communication with the inlet 152 is supported at a central portion of the disk-shaped member 164.

The conduits 150 typically have a non-rectangular grid arrangement. Preferably, each of the branches of the tree topology formed by the conduits 150 includes a portion of a conduit oriented along a radial axis of the disk-shaped member. More generally, the conduits 150 include a first conduit 170 having a first portion 172 oriented along a first radial axis 174 and a second conduit 180 having a second portion 182 oriented along a second radial axis 184. The first radial axis 174 is transverse to the second radial axis 184. Further, the first radial axis 174 and the second radial axis 184 intersect at a central portion, and preferably at a center point 190, of the disk-shaped member 164.

The inlet 152 receives a sample of a plurality of molecules, which may be processed and/or noninvasively extracted. The sample is communicated to inlet 152 either centrifugally or electrophoretically.

The disk-shaped member 164 is rotated to create a centrifugal force. The centrifugal force communicates the sample through conduits associated with each of the branches of the tree topology. A respective distributed portion of the sample is communicated to each of the molecular detection chambers 156 via its respective one of the outlets 154. Additionally, the centrifugal force communicates ligase from the ligase chamber 162 to each of the molecular detection chambers 156.

Preferably, each of the molecular detection chambers 156 includes both immobilized molecular probes and unbound molecular probes as described earlier. The immobilized molecular probes can differ between pairs of the molecular detection chambers 156. Similarly, the unbound molecular probes can differ between pairs of the molecular detection chambers 156. In this way, each of the molecular detection chambers 156 can be used to detect a respective one of a plurality of potential molecular structures in the sample. For example, four adjacent molecular detection chambers 156 can be used to detect and identify a single base mutation in the sample. Generally, a molecular structure in the sample is detectable for each molecular detection chamber 156 and its associated chamber 160 using the method described with reference to FIG. 8.

Figure 10:
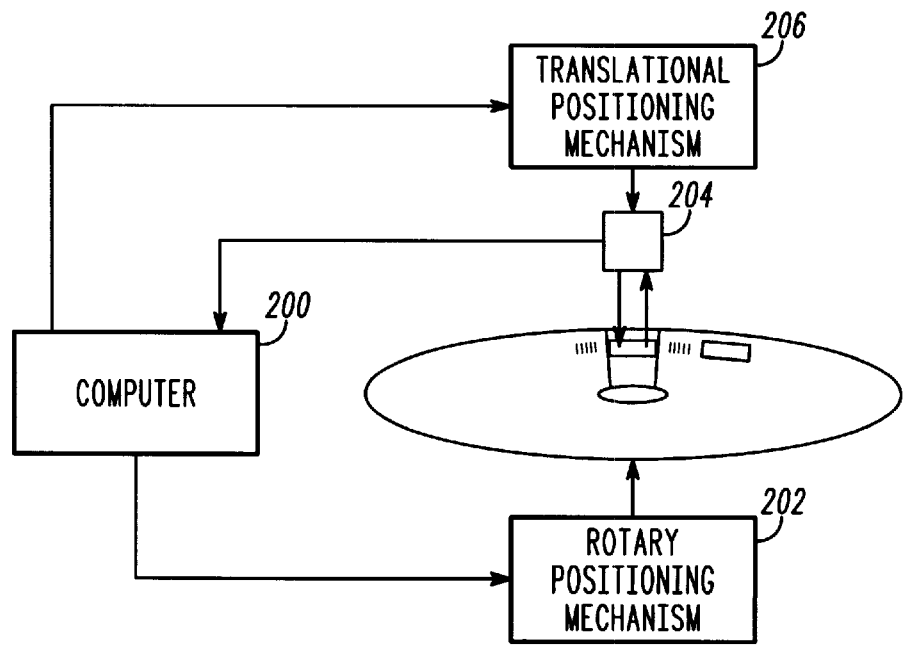
FIG. 10 is a schematic block diagram of a system for performing a molecular detection method using embodiments of the molecular detection apparatus described herein.

FIG. 10 is a schematic block diagram of a system for performing a molecular detection method using embodiments of the molecular detection apparatus described herein. The system includes a processing apparatus such as a computer 200 that receives a program defining appropriate high-level steps to be executed in the method. The computer 200 translates or compiles the program into lower-level steps executable by a sequential series of stages. The lower-level steps can include steps to control an angular speed (e.g. to generate a centrifugal force) and/or an angular position of a rotary positioning mechanism 202 (such as a motor), to control an open or a closed state of a valve or a gate of the apparatus, to control an electric field generated in the apparatus, to sense for molecules using a sensing head 204, and/or to position the sensing head 204 along a radial axis of the apparatus with a translational positioning mechanism 206. The computer 200 executes the lower-levels steps to perform the method.

The computer 200 processes quantities sensed by the sensing head 204 to generate one or more decision quantities. The decision quantities indicate the presence or absence of molecular structures in the sample. The computer 200 generates an output, such as a visual output for a display device or a machine-readable output for a machine-readable storage medium, based upon the decision quantities.

Preferably, the sensing head 204 includes an optical sensor to sense fluorescent tags in the apparatus. The sensing head 204 can also serve to sense embedded information from the apparatus. The embedded information can include information identifying the molecular structure and/or the molecular probes associated with each molecular detection chamber. If desired, the embedded information associated with a molecular detection chamber can be located adjacent thereto. As another option, the embedded information can encode the steps to be executed by the computer 200. Preferably, the embedded information is encoded by optical data readable by the sensing head 204. Optionally, the optical data can include a bar code.

It is noted that the herein-described system can be constructed and/or modified in accordance with the teachings in the above-listed patent applications incorporated by reference herein. Further, the herein-described embedded information can be stored in accordance with the teachings in the above-listed patent applications.

It is also noted that alternative enzymes can be substituted for the ligase in alternative embodiments of the present invention. Further, it is noted that alternative sample extraction devices can be substituted for the noninvasive extraction device described herein.

Any of the chambers described herein can include a temperature control element such as a resistor or another heating element to control a temperature therein. For example, the chamber 82 can have an associated heating element to thermally dissociate molecules therein.

Still further, it is noted that embodiments of the present invention are amenable for repeated use. For example, after performing a molecular detection process as described earlier using a first sample, the apparatus can be washed to flush materials including one or more of sample molecules, probes, ligase, and other reagents. Thereafter, the chambers are refilled with reagents such as probes and/or ligase. The reagents can be dispensed into the chambers using a liquid dispensing head, for example.

If desired, some reagents used for the first sample can be retained for use with subsequent samples. For example, some of the probes can be retained in the apparatus for subsequent use. Additionally, an amount of ligase in the ligase chamber can be sufficient to perform more than one molecular detection process.

Once prepared for reuse, the molecular detection process as described earlier can be performed using a second sample. To perform the molecular detection process for the second sample, the computer 200 can perform the same steps as for the first sample, or can perform different steps than for the first sample.

Thus, there has been described herein several embodiments including preferred embodiments of a molecular detection apparatus and method.

Embodiments of the present invention provide a differential sensing approach to molecular detection which may improve the detection sensitivity.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A molecular detection apparatus comprising:

a sample-receiving inlet;

a plurality of outlets;

a plurality of conduits interconnected in a tree topology to couple the inlet with the plurality of outlets, the plurality of conduits providing a plurality of branches of the tree topology, wherein the plurality of conduits includes a first conduit and a second conduit, the first conduit having a first portion oriented along a first radial axis, the second conduit having a second portion oriented along a second radial axis transverse to the first radial axis, wherein the inlet is located at a root vertex of the tree topology, wherein each of the plurality of outlets is located at a corresponding leaf vertex of the tree topology, and wherein the tree topology has a height of at least two;

a plurality of molecular detection chambers, each of the plurality of molecular detection chambers coupled to a respective one of the plurality of outlets;

a plurality of radially-oriented conduits; and a plurality of chambers, each of the plurality of chambers coupled to a respective one of the plurality of molecular detection chambers by a respective one of the plurality of radially-oriented conduits, wherein each of the plurality of chambers is more distant from the inlet than its respective one of the plurality of molecular detection chambers.

2. The molecular detection apparatus of claim 1 further comprising a disk-shaped member to support the plurality of conduits, wherein each of the plurality of radially-oriented conduits is oriented about a respective one of a plurality of radial axes, and wherein the first radial axis, the second radial axis, and the plurality of radial axes intersect at a central portion of the disk-shaped member.

3. The molecular detection apparatus of claim 1 wherein the plurality of outlets includes at least four outlets.

4. The molecular detection apparatus of claim 1 wherein the plurality of outlets includes at least six outlets.

5. The molecular detection apparatus of claim 1 wherein the plurality of conduits have a non-rectangular grid arrangement.

6. The molecular detection apparatus of claim 1 further comprising a ligase chamber coupled to at least one of the plurality of conduits.

7. The molecular detection apparatus of claim 1 further comprising a plurality of molecular probes, wherein each of the plurality of molecules detection chambers has at least one of the plurality of molecular probes immobilized therein.

8. A molecular detection apparatus comprising:

a sample-receiving inlet;

a noninvasive extraction device in communication with the inlet, the noninvasive extraction device including an ultrasonic emitter;

a plurality of outlets;

a plurality of conduits interconnected in a tree topology to couple the inlet with the plurality of outlets, the plurality of conduits providing a plurality of branches of the tree topology, wherein the inlet is located at a root vertex of the tree topology, wherein each of the plurality of outlets is located at a corresponding leaf vertex of the tree topology, and wherein the tree topology has a height of at least two; and a plurality of molecular detection chambers, each of the plurality of molecular detection chambers coupled to a respective one of the plurality of outlets.

9. The molecular detection apparatus of claim 8 further comprising a disk-shaped member to support the inlet, the plurality of outlets, the plurality of conduits, the plurality of molecular detection chambers, and the noninvasive extraction device, wherein the noninvasive extraction device is located at a central portion of the disk-shaped member.

10. The molecular detection apparatus of claim 8 further comprising a plurality of molecular probes, wherein each of the plurality of molecules detection chambers has at least one of the plurality of molecular probes immobilized therein.

11. A molecular detection apparatus comprising:

a disk-shaped support member;

a first sample-processing device supported by the disk-shaped support member, the first sample-processing device having an elongate portion oriented along a first radial axis of the disk-shaped support member;

a second sample-processing device supported by the disk-shaped support member, the second sample-processing device having an elongate portion oriented along a second radial axis of the disk-shaped support member, wherein the second radial axis is transverse to the first radial axis; and a noninvasive extraction device located at a center portion of the disk-shaped support member, the noninvasive extraction device in communication with the first sample-processing device and the second sample-processing device, the noninvasive extraction device including an ultrasonic emitter.

12. The molecular detection apparatus of claim 11 wherein the first sample-processing device includes a first sample-purification stage, a first sample-amplification stage, a first tagging stage, a first processing stage, and a first collection stage, and wherein the second sample-processing device includes a second sample-purification stage, a second sample-amplification stage, a second tagging stage, a second processing stage, and a second collection stage.

13. The molecular detection apparatus of claim 12 wherein the first sample-processing device and the second sample-processing device are removably supported by the disk-shaped support member.

* * * * *